United States Patent [19]

Pierantozzi et al.

[11] Patent Number: 4,996,322

[45] Date of Patent: Feb. 26, 1991

[54] SEPARATION OF AMIDES WITH MOLECULAR SIEVES

[75] Inventors: Ronald Pierantozzi, Orefield; Mildred A. Miller, N. Catasauqua; Mark L. Listemann, Whitehall; Thomas R. Gaffney, Allentown; Charles G. Coe, Macungie, all of Pa.

[73] Assignee: Air Products and Chemicals, Inc., Allentown, Pa.

[21] Appl. No.: 351,987

[22] Filed: May 15, 1989

[51] Int. Cl.$^5$ ............................................. C07C 233/03
[52] U.S. Cl. ................................................... 564/216
[58] Field of Search ......................................... 564/216

[56] References Cited

U.S. PATENT DOCUMENTS

| | | | |
|---|---|---|---|
| 4,139,572 | 2/1979 | Miwa et al. | 260/674 |
| 4,334,097 | 6/1982 | Schmidt | 564/201 |
| 4,444,986 | 4/1984 | Dessau | 585/820 |
| 4,567,300 | 1/1986 | Murao et al. | 564/215 |
| 4,575,434 | 3/1986 | Frank et al. | 558/435 |
| 4,578,515 | 3/1986 | Dawson et al. | 564/215 |
| 4,633,018 | 12/1986 | Zinnen | 564/264 |
| 4,714,783 | 12/1987 | Zinnen et al. | 568/434 |

FOREIGN PATENT DOCUMENTS

| | | |
|---|---|---|
| 6828087 | 4/1987 | Australia . |
| 61-28969 | 12/1986 | Japan . |
| 62-195352 | 3/1987 | Japan . |
| 62-59248 | 8/1987 | Japan . |
| 724500 | 3/1980 | U.S.S.R. . |

OTHER PUBLICATIONS

S. A. Tahoun and M. M. Mortland, "Complexes of Montmorillonite with Primary, Secondary, and Tertiary Amides: I. Protonation of Amides on the Surface of Montmorillonite," Soil Science 102(4), pp. 248–254, and 10(5), pp. 314–321 (1966).

R. M. Barrer, "Zeolites and Clay Minerals as Sorbents and Molecular Sieves," pp. 5–14, Academic Press, (1978).

D. W. Breck, "Adsorption by Dehydrated Zeolite Crystals," Zeolite Molecular Sieves, pp. 633–645 and 699–709, Kruger Publishing Co., Malabar, Florida (1984).

D. M. Ruthven, "Zeolites as Selective Adsorbents," Chemical Engineering Process, pp. 42–50, Feb. 1988.

Primary Examiner—Richard L. Raymond
Assistant Examiner—Mark W. Russell
Attorney, Agent, or Firm—Mark L. Rodgers; William F. Marsh; James C. Simmons

[57] ABSTRACT

Amides having different molecular kinetic diameters or heats of adsorption, such as formamide and N-(1-alkoxyethyl)formamide, are separated under mild conditions with a molecular sieve which selectively adsorbs one of the amides, such as formamide. N-vinylformamide can be purified by removing formamide remaining in synthesis process streams using this technique. The adsorbed amide can be desorbed by heating the molecular sieve in either inert or reactive atmospheres. Preferred molecular sieves include the zeolites of types A, X, Y, molecular sieves of the MFI topology, chabazite, and mordenite. Calcium chabazite is particularly versatile and effective.

19 Claims, No Drawings

SEPARATION OF AMIDES WITH MOLECULAR SIEVES

FIELD OF THE INVENTION

This invention relates to a method of separating at least two amides by using a molecular sieve to selectively adsorb one of the amides. In another aspect it relates to a process for reducing the amount of formamide which would otherwise contaminate N-vinylformamide which has been prepared by a synthesis route in which formamide is one of the starting reactants.

BACKGROUND OF THE INVENTION

Amides having from 1 to about 10 carbon atoms are useful in preparing pharmaceuticals, agricultural chemicals and various polymers. For example poly(vinylamine) is a valuable polymer which is best prepared by hydrolysis of the polymer formed on polymerization of N-vinylformamide which in turn is prepared form a number of precursors, all of which are synthesized from formamide. The purity of any of the amide products presents a problem in downstream reactions and this is especially true in the case of N-vinylformamide which contains residual quantities of formamide. Separation of formamide from N-vinylformamide or from any of its precursors, such as N-(1-ethoxyethyl)formamide, is complicated by the polar nature of the compounds, their high boiling points which typically exceed 200° C., and the thermal instability of the vinyl product and its precursors. In general, the art lacks suitable commercial methods for low temperature, non-distillation separation methods for purifying amides.

U.S. Pat. No. 4,334,097, Schmidt (1982), discloses preparation of N-($\alpha$-alkoxyalkyl)carboxamides which are useful intermediates in making N-vinyl-carboxamides, e.g., N-vinyl-N-methylacetamide, which can be polymerized to give valuable polymers. The N-($\alpha$-alkoxyalkyl)carboxamide is made by reacting a carboxylic acid amide with $\alpha$-halogenoalkyl ethers in the presence of tertiary amines. Separations are performed by solvent extractions and distillations.

Japanese Patent Application No. 60-129132, Sato et al. (1985), discloses the separation of low levels of formamide from N-vinylformamide using solvent extraction. This process requires large quantities of aromatic hydrocarbon and the disposal of aqueous formamide waste streams.

Japanese Patent Application No. 61-28969, Sato et al. (1986), describes separating formamide from N-vinylformamide by extraction wit water and an aromatic hydrocarbon. The N-vinylformamide is recovered from the organic phase.

U.S. Pat. No. 4,567,300, Murao et al. (1986), describes making N-substituted formamides from formamide and acetaldehyde using a basic catalyst and, optionally, further reacting an alcohol in the presence of an acid catalyst to form N-(1-hydroxyethyl)formamide and N-(1-alkoxyethyl)formamide which are intermediates for N-vinylformamide. Separation of products is performed by crystallization from solution and filtration.

U.S. Pat. No. 4,578,515, Dawson et al. (1986), describes preparing ethylidene bisformamide from acetaldehyde and formamide in the presence of an acidic catalyst and an ammonia scavenger. Bisformamide is recovered by distillation and can be cracked to make N-vinylformamide, a monomer for useful polymers, such as poly(vinylamines). Thin film evaporation techniques are used because of the sensitivity of ethylidene bisformamide to high temperatures. The acid catalyst can be an acidic ion exchange resin such as sulfonated polystyrene cross-linked with divinylbenzene.

Australian Patent Application Number 68280/87, Kroenar et al. (1987), describes purifying N-vinylformamide by fractional distillation in the presence of formamide under reduced pressure so that formamide is present in the distillate. The presence of formamide during the distillation is said to avoid formation of popcorn polymer. This process requires expensive apparatus, low pressure operation and the recycle of large amounts of formamide.

Japanese Patent Application Number 62-195352, Sato et al. (1987), describes recovery of N-vinylformamide from a mixture formed on thermal decomposition of N-($\alpha$-alkoxyethyl)formamide by distillation in which acid is added to adjust the pH. This process also requires operation at low pressure and short residence times.

Japanese Patent Application Number 62-59248, Tamaru et a. (1987), discloses the production of N-vinylformamide by reacting acetaldehyde and formamide to form N-($\alpha$-hydroxyethyl)formamide which is then reacted with a polyhydric alcohol followed by thermal decomposition. The product is purified by distillation. This process requires recycle of large amounts of diol and the efficiency of the final separation of diol and N-vinylformamide has not been adequately demonstrated.

As indicated by the reference cited above, although the problems of separating amides one form another have existed for several years, there has been no suggestion or indication that amides could be separated effectively by using molecular sieves.

Tahoun, et al., *Soil Science* 102(4), pp. 248–54 and 102(5), pp. 314–21 (1966), discuss detection of complexes of primary, secondary and tertiary amides bonded on clay surfaces but do not suggest using the clay (montmorillonite) to separate one amide from another.

Barrer, R. M., *Zeolites and Clay Minerals as Sorbents and Molecular Sieves*, pp. 5–14, Academic Press (1978), gives a survey of the sorption potential of various zeolites, including types A, X, Y and ZK-5, as well as natural zeolites, such as chabazite. The presence of cations, such as Na and Ca, is said to change the molecular sieving properties of a zeolite. Separations described for chabazite include methanol from acetone; methanol, carbon disulfide and acetonitrile from benzene; ethanol from toluene; ethanol and water from diethyl ether; sulfur dioxide from chloroform; hydrogen sulfide from benzene; ethanol and methylamine form trimethylamine; ethylamine from diethylamine; acetonitrile from thiophene, hydrogen chloride form chloroform; methylene chloride from dioxane; and methylene bromide from benzene. Calcium chabazite is said to have the ability to separate n-paraffins from branched chain paraffins, cycloparaffins, and aromatic hydrocarbons, but there is no suggestion to use zeolites to separate amides.

U.S. Pat. No. 4,139,572, Miwa et al. (1979), describes separating para-xylene from other $C_8$ aromatic hydrocarbons using a crystalline aluminosilicate adsorbent, e.g., X or Y zeolites and desorbing the para-xylene with a 1-(lower alkyl)-4-isopropylbenzene.

USSR Certificate of Invention No. 724,500, Akhmadeev et al. (1980), describes a process for removing amides from dimethylformamide using, as a sorbent, activated carbon modified with boric acid. This method is said to be an improvement over purification of dimethylformamide by adsorption of impurities on silica gel or ion exchange resins followed by distillation in the presence of a non-volatile acid, water and an extractant, in which the degree of purification of product is rather low.

Breck, "Adsorption by Dehydrated Zeolite Crystals", Zeolite Molecular Sieves, pp 633–645 and 699–709, Kruger Publishing Co., Malabar, FL (1984), provides a thorough discussion of the molecular sieve effect of zeolite crystals, including the effect of various cations on adsorption performance. Also described is the use of various zeolites commerically for separation of mixtures, particularly the use of types A and X, mordenite, chabazite and erionite. The separations include drying, desulfurization, dewaxing, normal paraffin separation for detergent manufacture, hydrogen and hydrogen sulfide recovery, olefin recovery and air separation. Drying dimethylformamide is listed but there is no disclosure of separating one amide form another.

U.S. Pat. No. 4,633,018, Zinnen (1986), discloses use of a Y type zeolite cation exchanged with Ca or Ni, an X type zeolite cation exchanged with Ni, Ca, Ba, K or Na, or an L type zeolite exchanged with K for separating 2,4-toluenediamine from 2,6-toluenediamine. Reference is made to a co-pending application disclosing separation of 2,3- and 3,4-dinitrotoluene from 2,4- and 2,6-dinitrotoluene using a Ca or Na exchanged Y type zeolite. Another referenced application mentions separating 2,4-toluenediisocyanate and 2,6-toluenediisocyanate with a Y zeolite.

U.S. Pat. No. 4,575,434, Frank et al. (1986), describes a method of purifying nitriles by removing tallow amides (average molecular weight of 270) with layered aluminosilicates having exchangeable alkaline or alkaline earth cations after protonating the amides with an acid.

U.S. Pat. No. 4,714,783, Zinnen, et al. (1987), discloses separating isomers of nitrobenzaldehydes by selective adsorption on X or Y zeolites. An X-type zeolite containing sodium or lithium cations selectively adsorbs meta-nitrobenzaldehyde in preference to the para- and ortho-isomers. A Y-type zeolite having alkali metal or alkaline earth metal cations selectively adsorbs the ortho-nitrobenzaldehyde. Methyl acetate and ethyl acetate can be used as desorbents.

Ruthven, "Zeolites as Selective Adsorbents", Chem. Engr. Progress, pp. 42–50, Feb. 1988, describes the use of zeolites as adsorbents in making separations between hydrocarbons, carbohydrates and oxygen and nitrogen. The role of adsorbent pore size in selective separations is discussed and general procedures are given for adsorption processes and adsorbent regeneration. There is no disclosure on separation of amides.

BRIEF DESCRIPTION OF THE INVENTION

We have found that molecular sieves can be used very effectively for separating lower molecular weight amides from each other or form amides having higher molecular weight, but in which the amides to be separated have different molecular kinetic diameters or different heats of adsorption. The process is carried out by forming a solution which contains the amides to be separated, or the solution may pre-exist as a part of a process stream. The solution is contacted with a molecular sieve which has pore openings large enough to admit at least one of the amides, thereby selectively sorbing one of the amides on the basis of size or heat of adsorption. The amide selectively adsorbed is the one having the smaller molecular kinetic diameter or the larger heat of adsorption. Since amides have higher heats of adsorption on molecular sieves containing cations or acid sites, such molecular sieves show higher selectivity. The solution then is separated from the molecular sieve which contains the sorbed amide.

Our invention is especially valuable as a method for reducing the amount of formamide which would otherwise be present in the product N-vinylformamide which has been prepared by a synthesis procedure in which formamide is used as one of the starting reactants. In this process the solution which contains residual formamide and either the N-vinylformamide or an amide precursor thereof, is contacted with a molecular sieve, such as zeolite A, X or Y, a molecular sieve of the MFI topology, chabazite, mordenite, or clay, thereby sorbing the formamide in the molecular sieve and, thereafter, separating the molecular sieve from the solution. In connection with our invention, we have discovered quite unexpected behavior of the zeolite, calcium chabazite, which has been shown to be very effective in separating a wide variety of amides in a relatively short period of time with high selectivity for the more strongly adsorbed amide.

DETAILED DESCRIPTION OF THE INVENTION

This invention is a process which enables the separation of less substituted amides from more substituted amides and in particular is valuable in the separation of formamide from N-vinylformamide or one of its precursors such as N-(1-ethoxyethyl)formamide. In general, the process is useful for separating lower amides, for example amides having form 1 to 3 and preferably 1 or 2 carbon atoms per molecule, from each other or form other amides which have a higher molecular weight, for example amides containing 3 to 10 carbon atoms per molecule. These compounds are generally difficult to separate by distillation because of their sensitivity to high temperatures and because of their relatively high boiling points may require subatmospheric pressures to carry out distillation separations. The amides can be separated by our invention provided they have different molecular kinetic diameters or different heats of adsorption, so that one of the amides is preferentially sorbed on the molecular sieve. The molecular sieve has pore openings which are at least large enough to accommodate formamide. For example, formamide can be separated from N-vinylformamide or from one of its precursors such a N-(1-methoxyethyl)formamide or N-(1-ethoxyethyl)formamide or from N-methylformamide or N,N-dimethylformamide. Other lower amides can also be separated from higher molecular weight amides such as N-methylformamide from N-N-dimethylformamide or the separation of acetamide form N-methylacetamide. Higher molecular weight amides which are also excluded form the molecular sieve because of the size-restricted pore openings but which are nevertheless soluble in the solvent used, can be present and are separated from the lower amides by this procedure.

The amide mixture to be separated is either dissolved in a solvent or a solution of the amides may be already present as a process stream in the synthesis of an amide product. Suitable solvents include ethanol, tetrahydrofuran, methyl tertiarybutyl ether, and the like, although any non-polar to moderately polar solvent is acceptable. Small, highly polar solvents, such as water, should be avoided, although, as demonstrated in the examples, water can be present in a small excess over that adsorbed by the molecular sieve without adversely affecting the separation of the amides. Generally if water is present, additional molecular sieve will be required in order to reduce the water content to a level which is not deleterious.

The solution of amides is contacted with the molecular sieve sorbent for about 0.01 to 48 hours under atmospheric or autogenous pressure. Generally the sorbent is initially calcined in air at elevated temperatures, for example 400° C.

The molecular sieves which can be used are well known for their effectiveness in separating paraffins, alcohols and various gases as indicated by the patent and literature references cited above. Both naturally occurring and synthetic molecular sieves are useful in this invention. These molecular sieves include zeolites, aluminophosphates (ALPO), the related substituted materials, metal aluminophosphates (MeAPO), metal aluminosilicates (MeAPSO), other element substituted aluminophosphates (ElAPO), other element substituted aluminophosphosilicates (ElAPSO), silicaluminophosphates (SAPO), and clays. For a description of these molecular sieves, see Flanigen, et al., *New Developments in Zeolite Science and Technology*, pp 103–112, Elsevier Kodonsha (1986). Preferably, however, the molecular sieve to be used in this process is a cation-containing zeolite which is selected from types A, X, Y, MFI structured zeolites, chabazite or mordenite, as these sieves have been proven to be effective for a broad spectrum of amide separations. Examples of MFI structured zeolite include ZSM-5 and ZSM-11. The selection of the best molecular sieve in each case will depend upon the particular separation to be carried out. For example, when separating two amides, one of which has a molecular kinetic diameter larger than the other, it is desirable to use a molecular sieve containing cations or acid sites which are inaccessible to the larger of the two amides, as illustrated in the Examples.

We have discovered that the most versatile of the molecular sieves is a chabazite which contains divalent cations such as calcium chabazite or copper chabazite. Type X zeolite containing sodium cations is very effective for separating formamide from N-(1-ethoxyethyl)-formamide, which is one of the precursors for N-vinylformamide. Good results are also obtained with a type X zeolite containing calcium cations for the separation of formamide from N-(1-alkoxyethyl)formamides, particularly those formamides which contain alkoxy groups containing 1 or 2 carbon atoms. Type A zeolite containing sodium cations is especially useful in separating formamide from N-methylformamide or N,N-dimethylformamide. Type A zeolite containing sodium or calcium cations is also useful for separating formamide from N,N-dimethylformamide. Type X zeolite containing sodium cations is selective for separating acetamide from N-methylacetamide.

As indicated, the most versatile of the zeolites has been found to be a chabazite containing calcium cations. This molecular sieve is very effective if the contact time between the solution and the sorbent is relatively low, for example on the order of about 1 to 5 hours, and even shorter contact times can be used by altering the contacting procedure, such as by using a fixed bed of adsorbent.

Following sorption of the selected lower amide, the molecular sieve is separated from the solution and can be treated to remove the sorbed amide either for recovery and reuse in the process, or in order to enable the molecular sieve to be reused for further absorption separation. A suitable regeneration technique is to heat the molecular sieve under a subatmospheric pressure. Also a gas purge can be used.

The invention is further demonstrated by the following examples which state the selectively which has been found to result for the separation of different amide pairs. In these examples, unless otherwise stated, all adsorbents were calcined in air at 400° C. prior to use. These examples outline the effect of sorbent structure and cation content and charge on the separation of different amides. The examples also address the effect of water on formamide sorption, the maximum amount of formamide which can be sorbed by selected zeolites and a procedure for sorbent regeneration. Evaluation of the molecular sieves is based upon their demonstrated selectivity for removal of one of a pair of amides. The selectivity for the separation of component C, the more strongly sorbed amide, from component D, the less strongly sorbed amide, is defined as $$\text{Selectivity} = \frac{[\text{mole \% C/mole \% D}] \text{ adsorbed phase}}{[\text{mole \% C/mole \% D}] \text{ unadsorbed phase}}$$

Larger values for the selectivity indicate preferential sorption of C over D. The selectivity is sensitive to even small changes in the concentration of the minor component. Thus selectivities are best compared on an order of magnitude basis. In other words, a selectivity of 100 is significantly better than a selectivity of 10, but the difference between 10 and 20 is of limited consequence.

In the following examples (1–7) the major amide component is normalized to 100% and the baseline amount of the minor component is expressed as the 1% on a mole basis relative to the total moles of both amides in the system. The sorption data then show the amount of each amide remaining in the liquid phase after the specified time, relative to the baseline amounts of each amide. For example, if one begins with 100% of the major component and 16% of the minor component, and after time (t) finds 98% and 8%, respectively, remaining in the liquid phase, this means that of the initial number of moles of the major component, 2/100 or 2% of those moles were sorbed by the zeolite and 98% remain in solution. For the minor component, 8/16 or 50% of the initial moles were sorbed, and 8 of the original 16% remain in solution. To avoid infinite values in calculating selectivities, a value was assumed of at least 1% of component D in the absorbed phase even though the data show instances in which 100% of component D remained unadsorbed. The data are presented in this fashion to show the effectiveness of the sorbent at removing the minor component selectively in the presence of the major component.

EXAMPLE 1

This example demonstrates the separation of formamide ($H_2NCHO$) from N-(1-ethoxyethyl)formamide (EEF) using several different types of adsorbent in tetrahydrofuran (THF) solvent at 25° C. In all cases, unless otherwise indicated, 0.60 g adsorbent was treated with a solution containing $4.33 \times 10^{-3}$ mole (0.51 g) EEF and $8.66 \times 10^{-4}$ mole (about 0.04 g) of $H_2NCHO$ dissolved in 3.12 g THF. On a mole basis formamide is 17% of the total amides. The results of these separations are given in Table 1 which identifies each adsorbent, the time (t) of contacting in hours, the percent of each amide remaining in the solution after time t, the ratio of formamide remaining to the initial formamide present at t=0, and the selectivity of the separation as defined above.

TABLE 1

| Adsorbent | Time t (h) | % Remaining EEF | % Remaining $H_2NCHO$ | $\frac{H_2NCHO_t}{H_2NCHO_{t=0}}$ | Selectivity |
|---|---|---|---|---|---|
| Baseline | 0 | 100 | 17 | 1.00 | |
| KA | 1 | 99 | 16 | 0.96 | |
| | 5 | 99 | 16 | 0.96 | |
| | 21 | 99 | 10 | 0.59 | 70 |
| NaA | 1 | 100 | 16 | 0.94 | |
| | 5 | 98 | 15 | 0.86 | |
| | 21 | 100 | 9 | 0.55 | 90 |
| CaA | 1 | 100 | 5 | 0.30 | |
| | 5 | 100 | 2 | 0.12 | |
| | 21 | 100 | 2 | 0.12 | 750 |
| Lithium | 1 | 100 | 2 | 0.11 | |
| Chabazite | 5 | 100 | 2 | 0.11 | |
| | 21 | 99 | 2 | 0.11 | 740 |
| Potassium | 1 | 92 | 11 2[a] | 0.09 | |
| Chabazite | 5 | 94 | 2 | 0.09 | |
| | 23 | 95 | 1 | 0.08 | 340 |
| Calcium | 5 | 100 | 1 | 0.08 | ~1,500 |
| Chabazite | 21 | 100 | 3 | 0.16 | 470 |
| Ca-AW500[b] | 1 | 100 | 3 | 0.34 | |
| | 5 | 100 | 3 | 0.31 | |
| | 21 | 100 | 3 | 0.32 | 200 |
| Copper | 1 | 99 | <1[d] | <0.08 | |
| Chabazite[c] | 5 | 100 | <2 | <0.14 | |
| | 21 | 100 | <1 | <0.09 | >1,000 |
| NaX | 1 | 100 | 3 | 0.24 | |
| | 5 | 100 | 1 | 0.09 | |
| | 21 | 100 | <1 | <0.06 | >1,600 |
| KX | 1 | 95 | 9[a] | 0.47 | |
| | 5 | 93 | 9 | 0.47 | |
| | 23 | 93 | 6 | 0.29 | 30 |
| CaX | 1 | 100 | 5 | 0.28 | |
| | 5 | 98 | 3 | 0.20 | |
| | 21 | 100 | 2 | 0.13 | 750 |
| SrX | 1 | 95 | 4[a] | 0.23 | |
| | 5 | 94 | 3 | 0.17 | |
| | 23 | 93 | 2 | 0.12 | 110 |
| Calcium | 1 | 100 | 11 7[e] | 0.79 | |
| Mordenite | 5 | 100 | 3 | 0.34 | |
| | 23 | 100 | 3 | 0.32 | 200 |
| NaY | 1 | 100 | 2[a] | 0.11 | |
| | 5 | 100 | 2 | 0.11 | |
| | 23 | 100 | 2 | 0.11 | 850 |
| NaZSM-5 | 1 | 100 | 13 | 0.77 | |
| Si/Al = | 5 | 100 | 10 | 0.61 | |
| 14.7 | 21 | 100 | 11 | 0.66 | 50 |
| Silicate | 1 | 100 | 17 | 1.00 | |
| | 5 | 100 | 17 | 1.00 | |
| | 21 | 100 | 17 | 1.00 | <6 |
| LZY-62 | 1 | 100 | 2 | 0.11 | |
| | 5 | 100 | 2 | 0.11 | |
| | 23 | 100 | 2 | 0.11 | 790 |
| XN-1010[f] | 1 | 58 | 6 | 0.36 | |
| | 5 | 41 | 5 | 0.27 | |
| | 23 | 23 | 2 | 0.10 | — |
| HY[g] | 1 | 100 | 11 6[d] | 0.48 | |
| | 23 | 100 | 6 | 0.48 | 100 |
| ALPO-5[h] | 1 | 95 | 11[a] | 0.60 | |
| | 5 | 92 | 11 | 0.60 | |
| | 23 | 92 | 11 | 0.60 | 8 |
| SAPO-5[h] | 1 | 93 | 4[a] | 0.20 | |
| | 5 | 94 | 6 | 0.31 | |
| | 23 | 92 | 5 | 0.25 | 30 |
| Clay | 1 | 100 | 11 | 0.62 | |
| | 5 | 100 | 11 | 0.62 | |
| | 21 | 100 | 9 | 0.51 | 90 |
| $Al_2O_3$- | 1 | 97 | 15 | 0.87 | |
| pillared | 5 | 95 | 13 | 0.77 | |

TABLE 1-continued

| Adsorbent | Time t (h) | % Remaining EEF | % Remaining $H_2NCHO$ | $\frac{H_2NCHO_t}{H_2NCHO_{t=0}}$ | Selectivity |
|---|---|---|---|---|---|
| Clay | 21 | 95 | 11 | 0.64 | 10 |

[a]Initial amount of formamide eaquals $9.17 \times 10^{-4}$ mole (baseline value of 18%).
[b]Commercial material ion exchanged to contain ~80% calcium.
[c]Calcined to 250° C. under nitrogen.
[d]Baseline value of formamide equals 12%.
[e]Baseline value of formamide equals 9%.
[f]XN-1010 is a macroreticular high surface area (~540 $m^2$/g) sulfonic acid ion exchange resin available from Rohm and Haas.
[g]Calcined to 500° C. to convert the $NH_4^+$ form to the H+ form.
[h]Calcined to 400° C. under nitrogen.

Numerous sorbents are shown to be effective in selectively removing formamide from N-(1-ethoxyethyl)formamide (EEF). Three considerations for an efficient sorbent are (i) size selectivity, (ii) cation content, and (iii) cation accessibility. These are demonstrated by the data of Table 1.

For the A zeolites divalent cations are preferred over monovalent, although both are effective in the chabazites. Monovalent and divalent cation forms of the X and Y zeolites are equally effective. In general, cation charge is not a major issue in choosing a sorbent. Cation content is important, however. NaZSM-5 contains few cations and is markedly less effective than the A, chabazite, mordenite, X and Y zeolites. Among molecular sieves of the MFI topology, zeolites or cation-containing materials are preferred. The medium pore size of NaZSM-5 and silicalite should permit discrimination between formamide and EEF on the basis of size. This demonstrates that size selectivity alone is not always sufficient to separate amides.

Strongly acidic materials also selectively remove formamide, provided the acid sites are inaccessible to the EEF. Thus the acid form of a Y zeolite is moderately effective, while XN-1010 (a sulfonic acid resin) destroys much of the EEF. Calcined LZY-62 contains more $Na^+$ than does HY and is also more effective. This suggests that cations rather than protons are preferred, but, in general, both work.

Useful sorbents are not restricted to zeolites, as other molecular sieve materials, such as ALPOs, MeAPOs, MeAPSOs, ElAPOs, ElAPSOs, SAPOs and clays, meet the requirements outlined above. Note also that SAPO-5 has a higher cation content than ALPO-5 and is more effective. Preferred sorbents for the EEF/formamide separation are chabazites and NaX.

EXAMPLE 2

This example demonstrates the separation of formamide form N-(1-methoxyethyl)formamide (MEF) using several different adsorbent types, all of which are molecular sieves, in THF at 25° C. In each case, 0.60 g adsorbent was treated with a solution of $4.33 \times 10^{-3}$ mole MEF and $6.49 \times 10^{-4}$ mole formamide dissolved in 3.12 g THF. The results of these separations are given in Table 2 where data are presented in the same way as in Table 1.

TABLE 2

| Molecular Sieve | Time t (h) | % Remaining MEF | % Remaining $H_2NCHO$ | $\frac{H_2NCHO_t}{H_2NCHO_{t=0}}$ | Selectivity |
|---|---|---|---|---|---|
| Baseline | 0 | 100 | 18 | 1.00 | — |
| NaA | 1 | 99 | 14 | 0.91 | |
| | 5 | 98 | 13 | 0.89 | |
| | 21 | 100 | 12 | 0.79 | 50 |
| CaA | 1 | 100 | 10 | 0.65 | |
| | 5 | 98 | 4 | 0.29 | |

TABLE 2-continued

| Molecular Sieve | Time t (h) | % Remaining MEF | % Remaining H$_2$NCHO | $\frac{H_2NCHO_t}{H_2NCHO_{t=0}}$ | Selectivity |
|---|---|---|---|---|---|
| | 21 | 97 | <2 | <0.10 | 260 |
| CaX | 1 | 98 | 4 | 0.24 | |
| | 5 | 98 | 3 | 0.18 | |
| | 21 | 100 | <2 | <0.10 | 800 |
| NaX | 1 | 97 | 2 | 0.11 | |
| | 5 | 89 | 2 | 0.12 | |
| | 21 | 85 | 2 | 0.11 | 40 |
| Calcium Chabazite | 1 | 93 | <1 | <0.05 | |
| | 5 | 98 | <1 | <0.06 | |
| | 23 | 96 | <1 | <0.06 | 400 |

As shown by the data of Table 2, because of the large size difference between the formamide and MEF molecules, MEF/formamide separation follows the same trends as EEF/formamide separation shown in Example 1, although slightly more MEF is lost in NaX than was the case for EEF. Preferred sorbents include CaX and calcium chabazite.

EXAMPLE 3

This example shows the separation of formamide from N-vinylformamide (NVF) using several different types of molecular sieves in THF at 25° C., as in Examples 1 and 2. The N-vinylformamide was prepared by the high temperature elimination of ethyl alcohol (EtOH) from N-(1-ethoxyethyl)formamide and about 37% EtOH was present in the mixture to be separated. The results are shown in Table 3.

TABLE 3

| Molecular Sieve | Time t (h) | % Remaining NVF | % Remaining EtOH | % Remaining H$_2$NCHO | $\frac{H_2NCHO_t}{H_2NCHO_{t=0}}$ | Selectivity |
|---|---|---|---|---|---|---|
| Baseline | 0 | 100 | 37 | 23 | 1.00 | — |
| KA | 1 | 95 | 34 | 21 | 0.93 | |
| | 5 | 95 | 30 | 22 | 0.96 | |
| | 23 | 100 | 35 | 21 | 0.92 | ~10 |
| NaA | 1 | 100 | 41 | 10 | 0.44 | |
| | 5 | 93 | 26 | 3 | 0.14 | |
| | 23 | 93 | 28 | <1 | <0.04 | 200 |
| CaA | 1 | 99 | 40 | 17 | 0.76 | |
| | 5 | 91 | 24 | 11 | 0.46 | |
| | 23 | 89 | 22 | 2 | 0.10 | 80 |
| NaX | 1 | 100 | 34 | 6 | 0.26 | |
| | 5 | 95 | 39 | <2 | <0.1 | |
| | 23 | 87 | 25 | <2 | <0.08 | 70 |
| CaX | 1 | 100 | 45 | 13 | 0.57 | |
| | 5 | 100 | 33 | 11 | 0.48 | |
| | 23 | 83 | 16 | 6 | 0.25 | 10 |
| Calcium Chabazite | 1 | 93 | 21 | <1 | <0.05 | 200 |
| | 5 | 92 | 22 | <1 | <0.04 | |
| | 23 | 87 | 15 | <1 | <0.05 | 100 |

NVF is a much smaller molecule than EEF and losses are apparent in the X zeolites and the more accessible 8-ring zeolites, CaA and calcium chabazite. NaA is the preferred sorbent for this separation, although calcium chabazite provides equivalent results at shorter (1h) contact times.

EXAMPLE 4

This example shows separation of formamide from N-methylformamide (NMF) with various types of molecular sieves. In each case 0.60 g adsorbent was treated with a solution of $4.33 \times 10^{-3}$ mole NMF and $6.49 \times 10^{-4}$ mole formamide in 3.12 g THF at 25° C. The results are given in Table 4.

TABLE 4

| Molecular Sieve | Time t (h) | % Remaining NMF | % Remaining H$_2$NCHO | $\frac{H_2NCHO_t}{H_2NCHO_{t=0}}$ | Selectivity |
|---|---|---|---|---|---|
| Baseline | 0 | 100 | 12 | 1.00 | |
| NaA | 1 | 99 | 11 | 0.89 | |
| | 5 | 98 | 9 | 0.73 | |
| | 23 | 97 | 1 | 0.12 | 360 |
| CaA | 1 | 97 | 8 | 0.65 | |
| | 5 | 94 | 3 | 0.26 | |
| | 23 | 80 | <1 | <0.10 | 40 |
| CaX | 1 | 81 | 6 | 0.53 | |
| | 5 | 76 | 6 | 0.46 | |
| | 23 | 61 | 4 | 0.34 | 3 |
| NaX | 1 | 71 | 3 | 0.27 | |
| | 5 | 62 | 3 | 0.24 | |
| | 23 | 56 | 3 | 0.23 | 4 |
| Calcium Chabazite | 1 | 92 | <1 | <0.10 | |
| | 5 | 85 | <1 | <0.10 | |
| | 23 | 76 | <1 | <0.10 | 30 |

The data of Table 4 show the results of separations in which the amides differ only by a methyl group. In this case, zeolites A and chabazite, whose pre openings are defined by 8 membered rings, are superior to the X zeolites, whose pore openings are defined by 12 membered rings, with NaA being the preferred sorbent. Note again that calcium chabazite gives results almost as good at short contact times. This example clearly demonstrates the fine discrimination that can be accomplished with the proper choice of molecular sieve.

EXAMPLE 5

This example shows the separation of formamide from N,N-dimethylformamide (DMF) in which 0.60 g adsorbent was treated with a solution of $4.33 \times 10^{-3}$ mole DMF and $6.49 \times 10^{-4}$ mole formamide in 3.12 g THF at 25° C.

The results are given in Table 5.

TABLE 5

| Molecular Sieve | Time t (h) | % Remaining DMF | % Remaining H$_2$NCHO | $\frac{H_2NCHO_t}{H_2NCHO_{t=0}}$ | Selectivity |
|---|---|---|---|---|---|
| Baseline | 0 | 100 | 13 | 1.00 | |
| NaA | 3 | 99 | 7 | 0.52 | |
| | 5 | 99 | 5 | 0.41 | |
| | 50 | 100 | <1 | <0.10 | >1,200 |
| CaA | 3 | 100 | <1 | <0.10 | |
| | 5 | 100 | <1 | <0.10 | |
| | 50 | 100 | <1 | <0.10 | >1,200 |

TABLE 5-continued

| Molecular Sieve | Time t (h) | % Remaining DMF | % Remaining H₂NCHO | $\frac{H_2NCHO_t}{H_2NCHO_{t=0}}$ | Selectivity |
|---|---|---|---|---|---|
| CaX | 3 | 75 | 8 | 0.58 | |
| | 5 | 72 | 2 | 0.17 | |
| | 50 | 61 | 2 | 0.18 | 9 |
| NaX | 3 | 87 | <1 | <0.10 | |
| | 5 | 87 | <1 | <0.10 | |
| | 50 | 80 | <1 | <0.10 | 50 |
| Calcium Chabazite | 1 | 100 | <1 | <0.10 | |
| | 5 | 100 | <1 | >0.10 | |
| | 23 | 100 | <1 | <0.10 | <1,200 |

In this example the DMF is just enough larger than NMF that the small pore A zeolites and chabazite discriminate extremely well, but the larger pore X zeolites are much less effective.

EXAMPLE 6

This example shows separation of N-methylformamide from N,N-dimethylformamide (DMF) in which 0.60 g adsorbent was treated with a solution of $4.33 \times 10^{-3}$ mole DMF and $6.49 \times 10^{-4}$ mole NMF in 3.12 g THF at 25° C.

The results are given in Table 6.

TABLE 6

| Molecular Sieve | Time t (h) | % Remaining DMF | % Remaining NMF | $\frac{NMF_t}{NMF_{t=0}}$ | Selectivity |
|---|---|---|---|---|---|
| Baseline | 0 | 100 | 13 | 1.00 | — |
| NaA | 1 | 100 | 13 | 0.97 | |
| | 5 | 99 | 12 | 0.94 | |
| | 21 | 99 | 10 | 0.80 | 30 |
| CaA | 1 | 99 | 12 | 0.94 | |
| | 5 | 100 | 11 | 0.84 | |
| | 21 | 99 | 7 | 0.52 | 80 |
| CaX | 1 | 75 | 5 | 0.42 | |
| | 5 | 70 | 5 | 0.38 | |
| | 21 | 65 | 5 | 0.37 | 3 |
| NaX | 1 | 93 | 10 | 0.42 | |
| | 5 | 91 | 3 | 0.23 | |
| | 21 | 86 | 1 | 0.08 | 70 |
| Calcium Chabazite | 1 | 100 | 8 | 0.59 | |
| | 5 | 100 | 2 | 0.19 | |
| | 23 | 100 | <1 | <0.08 | >1,200 |

As was shown in Examples 4 and 5, type A zeolites are more effective than X zeolites at not removing too much of the larger amide. Calcium chabazite is extremely well suited for this particular separation.

This example also demonstrates the generality of this invention for the separation of smaller amides from larger ones. Neither amide need be primary. Formamide removal is, however, an issue of current commercial concern.

EXAMPLE 7

This example shows the separation of acetamide from N-methylacetamide (NMA) in which 0.60 g adsorbent was treated with a solution of $4.33 \times 10^{-3}$ mole NMA and $6.49 \times 10^{-4}$ mole acetamide in 3.12 g THF at 25° C.

The results are given in Table 7.

TABLE 7

| Molecular Sieve | Time t (h) | % Remaining NMA | % Remaining Acetamide | $\frac{CH_3CONH_{2t}}{CH_3CONH_{2t=0}}$ | Selectivity |
|---|---|---|---|---|---|
| Baseline | 0 | 100 | 12 | 1.00 | |
| NaA | 1 | 100 | 12 | 1.00 | |
| | 5 | 100 | 12 | 0.99 | |
| | 21 | 100 | 12 | 0.99 | <4 |
| CaA | 1 | 100 | 12 | 0.99 | |
| | 5 | 100 | 12 | 0.99 | |
| | 21 | 100 | 12 | 0.98 | <4 |
| CaX | 1 | 92 | 7 | 0.56 | |
| | 5 | 90 | 5 | 0.43 | |
| | 21 | 85 | 4 | 0.30 | 10 |
| NaX | 1 | 95 | 5 | 0.42 | |
| | 5 | 98 | 3 | 0.27 | |
| | 21 | 91 | 2 | 0.13 | 50 |
| Calcium Chabazite | 1 | 100 | 11 | 0.95 | |
| | 5 | 100 | 11 | 0.92 | |
| | 23 | 100 | 11 | 0.88 | 9 |

The above data show that acetamide was too large to enter the pores of the 8 membered ring zeolites (A and chabazite), but the X zeolites are still able to discriminate between two very similar molecules. NaX is the preferred sorbent for this separation. This example demonstrates that these amide separations with molecular sieves will work for amides not derived form formamide.

Examples 1-7 show that it is possible to separate any less substituted amide $R^1 CONR^2R^3$ from any more substituted amide $R^4CONR^5R^6$, where the R groups can be H but at least one of the R groups is alkyl or aryl, as long as the steric contributions of groups $R^1$-$R^3$ result in a molecule with a smaller kinetic diameter than that obtained with $R^4$-$R^6$. Comparison of acetamide (Example 7) to formamide (Examples 1-5) further suggests there is an upper limit on $R^1$ (or $R^4$) even if $R^2$, $R^3$, $R^5$ and $R^6$ are sterically undemanding. Once the kinetic diameter of $R^1CONH_2$ exceeds the pore size of the largest available sorbents, separation of any $R^1CONH_2$ derivatives would be unlikely.

More specifically, these examples demonstrate the separation of formamide from substituted formamides $HCONR^1R^2$. Particular examples of industrial utility include separation of formamide from any larger amide having the general formula $HCONR^1R^2$ in which $R^1$=H or lower alkyl and $R^2$=CH₃CH(X), where X=NHCHO, OR where R=$C_1$-$C_8$ alkyl or aryl, OC(O)CH₃, CN, and the like, as well as separation of NVF and formamide.

EXAMPLE 8

This example shows the effect of water on formamide adsorption by zeolite molecular sieves. In each case 0.60 g adsorbent was treated with a solution of $8.66 \times 10^{-4}$ mole formamide and 0, $4.33 \times 10^{-3}$, $1.30 \times 10^{-2}$, and $2.60 \times 10^{-2}$ mole water for the 0, 1, 3, and 6 equivalents (x) runs, respectively, dissolved in 3.12 g THF at 25° C. The expression of water levels as equivalents (x) relative to the formamide is arbitrary and used for convenience in the Table.

The results are given in Table 8.

TABLE 8

| Molecular Sieve | Water Content (x) | Time t (h) | % Remaining H₂NCHO | $\frac{H_2NCHO_t}{H_2NCHO_{t=0}}$ |
|---|---|---|---|---|
| Baseline | 0 | 0 | 17 | 1.00 |
| NaA | 0 | 1 | <1 | <0.07 |
| | 0 | 5 | <1 | <0.05 |
| | 0 | 23 | <2 | <0.12 |
| Baseline | 1 | 0 | 18 | 1.00 |
| NaA | 1 | 1 | 11 | 0.59 |

TABLE 8-continued

| Molecular Sieve | Water Content (x) | Time t (h) | % Remaining H$_2$NCHO | $\frac{H_2NCHO_t}{H_2NCHO_{t=0}}$ |
|---|---|---|---|---|
| | 1 | 5 | 2 | 0.10 |
| | 1 | 23 | <1 | <0.07 |
| Baseline NaA | 3 | 0 | 19 | 1.00 |
| | 3 | 1 | 14 | 0.75 |
| | 3 | 5 | 12 | 0.62 |
| | 3 | 23 | 12 | 0.64 |
| Baseline NaA | 6 | 0 | 18 | 1.00 |
| | 6 | 1 | 18 | 0.99 |
| | 6 | 5 | 18 | 1.00 |
| | 6 | 23 | 18 | 1.03 |
| Baseline CaA | 0 | 0 | 17 | 1.00 |
| | 0 | 1 | <1 | <0.06 |
| | 0 | 5 | <1 | <0.06 |
| | 0 | 23 | <1 | <0.05 |
| Baseline CaA | 1 | 0 | 18 | 1.00 |
| | 1 | 1 | <1 | <0.05 |
| | 1 | 5 | <1 | <0.05 |
| | 1 | 23 | <1 | <0.05 |
| Baseline CaA | 3 | 0 | 19 | 1.00 |
| | 3 | 1 | 7 | 0.35 |
| | 3 | 5 | 6 | 0.33 |
| | 3 | 23 | 6 | 0.33 |
| Baseline CaA | 6 | 0 | 18 | 1.00 |
| | 6 | 1 | 14 | 0.75 |
| | 6 | 5 | 12 | 0.67 |
| | 6 | 23 | 14 | 0.78 |
| Baseline CaX | 0 | 0 | 17 | 1.00 |
| | 0 | 1 | <1 | <0.05 |
| | 0 | 5 | <1 | <0.08 |
| | 0 | 23 | <2 | <0.13 |
| Baseline CaX | 1 | 0 | 18 | 1.00 |
| | 1 | 1 | <1 | <0.05 |
| | 1 | 5 | <1 | <0.08 |
| | 1 | 23 | <1 | <0.07 |
| Baseline CaX | 3 | 0 | 19 | 1.00 |
| | 3 | 1 | 7 | 0.37 |
| | 3 | 5 | 7 | 0.39 |
| | 3 | 23 | 7 | 0.35 |
| Baseline CaX | 6 | 0 | 18 | 1.00 |
| | 6 | 1 | 15 | 0.86 |
| | 6 | 5 | 14 | 0.76 |
| | 6 | 23 | 16 | 0.88 |
| Baseline Calcium Chabazite | 0 | 0 | 17 | 1.00 |
| | 0 | 1 | <1 | <0.05 |
| | 0 | 5 | <1 | <0.03 |
| | 0 | 23 | <2 | <0.09 |
| Baseline | 1 | 0 | 18 | 1.00 |
| Calcium Chabazite | 1 | 1 | <1 | <0.08 |
| | 1 | 5 | <1 | <0.05 |
| | 1 | 23 | <1 | <0.04 |
| Baseline Calcium Chabazite | 3 | 0 | 19 | 1.00 |
| | 3 | 1 | 13 | 0.66 |
| | 3 | 5 | 9 | 0.45 |
| | 3 | 23 | 9 | 0.44 |
| Baseline Calcium Chabazite | 6 | 0 | 18 | 1.00 |
| | 6 | 1 | 15 | 0.81 |
| | 6 | 5 | 14 | 0.79 |
| | 6 | 23 | 12 | 0.69 |

This example demonstrates that formamide can be removed in the presence of an excess of water, but if too much water is present additional zeolite is required for complete formamide removal. The invention can be operated by using enough molecular sieve to remove all formamide and water in a single step, or by using a prebed of adsorbent to remove water before contact with the appropriate molecular sieve optimized for the desired amide separation.

Note that 3 equivalents of water represents a 39 wt. % loading relative to the zeolite (which typically would have a capacity of up to 32 wt. % water) but appreciable amounts of formamide are still sorbed. Thus a zeolite can display appreciable capacities for both molecules simultaneously. As noted in Example 9, below, some zeolites can sorb substantial weight percentages of formamide, but on a mole basis this loading is considerably less than that achieved with the lower molecular weight water.

EXAMPLE 9

Formamide dissolved in THF was adsorbed on various molecular sieves using the weight amounts indicated for each molecular sieve. Table 9 shows the maximum loading over various time intervals of formamide onto the molecular sieve. Table 9 also shows the ultimate formamide sorption relative to the cation content of the different zeolites.

TABLE 9

| Molecular Sieve (grams) | Time (h) | Initial H$_2$NCHO (Mmoles) | Final H$_2$NCHO (Mmoles) | Total N$_2$NCHO Sorbed (Mmoles) | Mmoles H$_2$NCHO/ g zeolite | g H$_2$NCHO/ g zeolite | Millequivalents of Charge Per Gram[a] | Formamides[b] Per Cation |
|---|---|---|---|---|---|---|---|---|
| Lithium Chabazite (0.5253) | 1 | 8.10 | 6.60 | 1.50 | 2.86 | 0.13 | | |
| | 5 | 8.10 | 6.40 | 1.70 | 3.23 | 0.15 | | |
| | 21 | 8.10 | 6.57 | 1.53 | 2.91 | 0.13 | 4.94 | 0.59 |
| Potassium Chabazite (0.6205) | 1 | 9.57 | 8.03 | 1.54 | 2.48 | 0.11 | | |
| | 5 | 9.57 | 7.91 | 1.65 | 2.67 | 0.12 | | |
| | 21 | 9.57 | 7.98 | 1.59 | 2.56 | 0.12 | 3.75 | 0.68 |
| Calcium Chabazite (1.2058) | 1 | 18.58 | 13.72 | 4.85 | 4.02 | 0.18 | | |
| | 5 | 18.58 | 13.31 | 5.27 | 4.37 | 0.20 | | |
| | 21 | 18.58 | 13.26 | 5.31 | 4.40 | 0.20 | 4.27 | 2.06 |
| NaA (1.2105) | 1 | 18.66 | 18.23 | 0.43 | 0.35 | 0.02 | | |
| | 5 | 18.66 | 17.63 | 1.03 | 0.85 | 0.04 | | |
| | 21 | 18.66 | 15.95 | 2.71 | 2.24 | 0.10 | | |
| | 48 | 18.66 | 15.05 | 3.61 | 2.98 | 0.13 | 7.00 | 0.43 |
| CaA (0.7866) | 1 | 12.12 | 10.86 | 1.26 | 1.60 | 0.07 | | |
| | 5 | 12.12 | 10.04 | 2.08 | 2.65 | 0.12 | | |
| | 21 | 12.12 | 8.72 | 3.40 | 4.32 | 0.20 | | |
| | 48 | 12.12 | 8.51 | 3.61 | 4.59 | 0.21 | 6.90 | 1.33 |
| NaX (1.2077) | 1 | 18.62 | 12.73 | 5.89 | 4.88 | 0.22 | | |
| | 5 | 18.62 | 12.34 | 6.28 | 5.20 | 0.23 | | |
| | 21 | 16.62 | 11.97 | 6.65 | 5.51 | 0.25 | | |
| | 48 | 18.62 | 12.28 | 6.34 | 5.25 | 0.24 | 6.41 | 0.82 |
| KX (1.2068) | 1 | 18.60 | 13.21 | 5.39 | 4.46 | 0.20 | | |
| | 5 | 18.60 | 11.86 | 6.74 | 5.58 | 0.25 | | |
| | 21 | 18.60 | 11.54 | 7.06 | 5.85 | 0.26 | 6.04 | 0.97 |
| CaX | 1 | 18.60 | 14.48 | 4.12 | 3.41 | 0.15 | | |

TABLE 9-continued

| Molecular Sieve (grams) | Time (h) | Initial H$_2$NCHO (Mmoles) | Final H$_2$NCHO (Mmoles) | Total N$_2$NCHO Sorbed (Mmoles) | Mmoles H$_2$NCHO/ g zeolite | g H$_2$NCHO/ g zeolite | Milliequivalents of Charge Per Gram[a] | Formamides[b] Per Cation |
|---|---|---|---|---|---|---|---|---|
| (1.2072) | 5 | 18.60 | 13.43 | 5.16 | 4.28 | 0.19 | | |
|  | 21 | 18.60 | 11.92 | 6.68 | 5.53 | 0.25 | | |
|  | 48 | 18.60 | 11.80 | 6.79 | 5.63 | 0.25 | 6.61 | 1.70 |
| SrX | 1 | 18.73 | 15.81 | 2.92 | 2.40 | 0.11 | | |
| (1.2145) | 5 | 18.73 | 14.71 | 4.02 | 3.31 | 0.15 | | |
|  | 21 | 18.73 | 12.55 | 6.18 | 5.09 | 0.23 | | |
|  | 48 | 18.73 | 11.64 | 7.09 | 5.83 | 0.26 | 6.04 | 1.93 |
| NaY | 1 | 11.77 | 7.24 | 4.89 | 6.39 | 0.29 | | |
| (0.7645) | 5 | 11.77 | 7.13 | 5.00 | 6.53 | 0.29 | 4.49 | 1.46 |
|  | 21 | 11.77 | 7.21 | 4.56 | 5.97 | 0.27 | | |
|  | 48 | 11.77 | 7.69 | 4.08 | 5.34 | 0.24 | 0.49 | 1.19 |
| NaZSM-5 | 1 | 13.52 | 11.56 | 1.96 | 2.23 | 0.10 | | |
| (0.8768) | 5 | 13.52 | 11.36 | 2.15 | 2.46 | 0.11 | 1.02 | 2.41 |
|  | 21 | 13.52 | 12.24 | 1.28 | 1.46 | 0.07 | | |
|  | 48 | 13.52 | 12.75 | 0.77 | 0.88 | 0.04 | 1.02 | 0.86 |
| Silicalite | 1 | 13.52 | 12.89 | 0.63 | 0.72 | 0.03 | | |
| (0.8778) | 5 | 13.52 | 12.51 | 1.01 | 1.15 | 0.05 | | |
|  | 21 | 13.52 | 13.49 | 0.03 | 0.03 | <0.01 | | |
|  | 48 | 13.52 | 13.52 | — | — | <0.01 | — | — |
| LZY-62 | 1 | 13.53 | 9.76 | 3.77 | 4.31 | 0.19 | | |
| (0.8748) | 5 | 13.53 | 9.54 | 3.99 | 4.56 | 0.20 | 4.71 | 0.97 |
|  | 21 | 13.53 | 10.06 | 3.47 | 3.97 | 0.18 | | |
|  | 48 | 13.53 | 10.34 | 3.19 | 3.65 | 0.16 | 4.71 | 0.77 |
| HY | 1 | 13.55 | 12.14 | 1.41 | 1.61 | 0.07 | | |
| (0.8775) | 5 | 13.55 | 11.97 | 1.58 | 1.80 | 0.08 | 4.65 | 0.39 |
|  | 21 | 13.55 | 12.55 | 1.00 | 1.14 | 0.05 | | |
|  | 48 | 13.55 | 13.12 | 0.43 | 0.49 | 0.02 | 4.65 | 0.11 |

[a] Calculated from the % Al$_2$O$_3$ determined by elemental analysis. meq charge/g = (wt % Al$_2$O$_3$/MW Al$_2$O$_3$) (2 moles Al/mole Al$_2$O$_3$) (1000 meq/eq)
[b] Calculated from mmol H$_2$NCHO per gram/mmol cations per gram at equilibrium.

The data of Table 9 demonstrate that selected zeolites can sorb considerable quantities of formamide under anhydrous conditions. The data of the two righthand columns show that the ratio of formamides per cation can vary appreciably for materials with similar cation contents on a weight basis. This suggests that not only is a high cation content important, but that the cations must be accessible to the formamide. Thus, although they have similar void volumes, NaX has twice the capacity of NaA, probably because a greater fraction of the cations are more accessible in the larger pore X zeolite. Note also that NaX and CaX have the same capacity. Comparison of the X zeolites to calcium chabazite suggests many of the cations in the X structure remain inaccessible in the presence of formamide, since chabazite appears to be an exceptionally accessible structure.

EXAMPLE 10

In order to demonstrate thermal desorption of formamide adsorbed by a molecular sieve and subsequent reuse of the zeolite for formamide adsorption, 0.60 g NaA zeolite initially calcined to 400° C. in air was treated with an excess of formamide in THF. The zeolite was divided into three portions, each portion was then regenerated thermally as indicated and again treated with an excess of formamide over various time intervals. The results in terms of formamide initially in the solution, remaining in solution after adsorption, and sorbed in the zeolite are given in Table 10.

TABLE 10

| Regeneration Procedure | Time (h) | Initial H$_2$NCHO (mole) | Final H$_2$NHCO (mole) | H$_2$NHCO Sorbed (mole) | mole H$_2$NHCO/ g zeolite | g H$_2$NHCO/ g zeolite |
|---|---|---|---|---|---|---|
| Fresh | 1 | $2.16 \times 10^{-3}$ | $2.11 \times 10^{-3}$ | $5.45 \times 10^{-5}$ | $9.09 \times 10^{-5}$ | 0.004 |
|  | 23 | $2.16 \times 10^{-3}$ | $8.19 \times 10^{-4}$ | $1.35 \times 10^{-3}$ | $2.24 \times 10^{-3}$ | 0.10 |
| 100° C. | 1 | $2.16 \times 10^{-3}$ | $1.05 \times 10^{-3}$ | $1.12 \times 10^{-3}$ | $1.86 \times 10^{-3}$ | 0.08 |
| Vacuum | 5 | $2.16 \times 10^{-3}$ | $1.14 \times 10^{-3}$ | $1.02 \times 10^{-3}$ | $1.71 \times 10^{-3}$ | 0.08 |
|  | 23 | $2.16 \times 10^{-3}$ | $5.77 \times 10^{-4}$ | $1.59 \times 10^{-3}$ | $2.64 \times 10^{-3}$ | 0.12 |
|  | 47 | $2.16 \times 10^{-3}$ | $4.01 \times 10^{-4}$ | $1.76 \times 10^{-3}$ | $2.94 \times 10^{-3}$ | 0.13 |
| 200° C. | 1 | $2.16 \times 10^{-3}$ | $9.50 \times 10^{-4}$ | $1.21 \times 10^{-3}$ | $2.02 \times 10^{-3}$ | 0.09 |
| Vacuum | 5 | $2.16 \times 10^{-3}$ | $1.05 \times 10^{-3}$ | $1.12 \times 10^{-3}$ | $1.87 \times 10^{-3}$ | 0.08 |
|  | 23 | $2.16 \times 10^{-3}$ | $8.08 \times 10^{-4}$ | $1.36 \times 10^{-3}$ | $2.26 \times 10^{-3}$ | 0.10 |
|  | 47 | $2.16 \times 10^{-3}$ | $5.21 \times 10^{-4}$ | $1.64 \times 10^{-3}$ | $2.74 \times 10^{-3}$ | 0.12 |
| 400° C. air | 1 | $2.16 \times 10^{-3}$ | $1.23 \times 10^{-3}$ | $9.33 \times 10^{-4}$ | $1.55 \times 10^{-3}$ | 0.07 |
| calcination | 5 | $2.16 \times 10^{-3}$ | $1.22 \times 10^{-3}$ | $9.46 \times 10^{-4}$ | $1.58 \times 10^{-3}$ | 0.07 |
|  | 23 | $2.16 \times 10^{-3}$ | $9.51 \times 10^{-4}$ | $1.21 \times 10^{-3}$ | $2.02 \times 10^{-3}$ | 0.09 |
|  | 47 | $2.16 \times 10^{-3}$ | $7.55 \times 10^{-4}$ | $1.41 \times 10^{-3}$ | $2.35 \times 10^{-3}$ | 0.11 | the calcium chabazite has a high formamide capacity and a high formamide to cation ratio. Although we are not to be bound by theory, this could explain why the chabazites reach equilibrium quickly and show excellent selectivities at short contact times. The calcium The data of Table 10 show that formamide sorbed under anhydrous conditions can be thermally desorbed at moderate temperatures. Should substantial quantities of water be present, higher temperatures will be required (e.g., 400° C. calcination is effective). Thus the invention can be operated to permit recovery or removal of the sorbed amide by thermal desorption or decomposition.

Identities and sources of adsorbents used in the foregoing examples are presented in Table 11.

TABLE 11

| Adsorbent | % Major Ion | Source |
|---|---|---|
| KA | 71 | As received from Linde Division of Union Carbide Corp. |
| NaA | 100 | As received from Linde Division of Union Carbide Corp. |
| CaA | 99 | Linde NaA exchanged with $CaCl_2$ |
| Lithium Chabazite | 82 (Si/Al = 2.3) | Ion exchanged with metal |
| Potassium Chabazite | 100 (Si/Al = 2.6) | chloride salt of synthetic |
| Calcium Chabazite | 100 (Si/Al = 2.6) | potassium chabazite |
| Ca AW-500 | 88 (Si/Al = 3.4) | Linde AW-500 with $CaCl_2$ |
| Copper Chabazite | 77 | $Cu(OAc)_2$ exchange of synthetic chabazite with Si/Al = 2.1 |
| NaX | 100 | Linde 13X |
| KX | 70 | Linde 13X exchanged with KCl |
| CaX | 99 | Linde 13X exchanged with $CaCl_2$ |
| SrX | 90 | Linde 13X exchanged with $SrCl_2$ |
| Calcium Mordenite | 60 | Norton Z-900 exchanged with $CaCl_2$ |
| NaY | 100 | Linde LZY-52 |
| NaZSM-5 | 100 | Template-free preparation giving a Si/Al = 29.3 |
| Silicalite | — | Linde S115 |
| HY | 80 | Linde LZY-62 (after 500° C. calcination) |
| HY | 100 | Linde LZY-82 |
| AlPO-5 | — | According to U.S. Pat. No. 4,310,440 |
| SAPO-5 | 100 | According to U.S. Pat. No. 4,440,871 |
| Clay | | Kaolinites and Bentonites, Georgia Kaolin Company |
| Pillard Clay | | Alumina Pillared Kaolinites and Bentonites (high montmorillonite content) |

As demonstrated by the above examples, the three components for an effective sorbent in an amide separation are (a) size selectivity, (b) cation content, and (c) cation accessibility.

Electric field gradients generated by the cations are advantageous to induce amide sorption, with metal cations being more effective than protons. Proton systems may operate by amide protonation (as is the case with acid treated carbons and clays) rather than through a gradient effect, as is the case with metal cations. Although size selectivity enhances discrimination between certain amides, this feature alone is not always sufficient to effect separation. Some zeolites are more efficient than others on a weight basis due to favorable siting of the cations. Formamide capacity is strongly influenced by water, although both molecules are strongly bound at certain sites in the zeolite.

Separation of high-boiling, thermally sensitive amides by distillation is known from the prior art to be difficult. Solvent extraction is a much milder process, but only works well for amides with substantially different solubility properties. The molecular sieve-based separation process of this invention is mild and very general, needing only a small size or adsorption energy difference between the molecules of the amides to be separated to operate efficiently.

Other embodiments and aspects of our invention will be apparent to those skilled in the art, without departing from the spirit or scope of the invention.

We claim:

1. A process for separating amides from each other which comprises forming a solution containing at least two amides of different molecular weights or different heats of adsorption wherein one amide has from 1 to 3 carbon atoms per molecule and a second amide has from 1 to 10 carbon atoms per molecule, contacting said solution with a molecular sieve selected from the group consisting of zeolites A, X, Y, chabazite, mordenite and mixtures thereof, having a preponderance of cations other than protons and having pore openings of a size sufficient to admit at least one of said amides, thereby selectively sorbing the amide having the lower molecular weight or the larger heat of adsorption.

2. A process in accordance with claim 1 wherein said molecular sieve containing the sorbed amide is separated from the solution containing the remaining amide.

3. The process of claim 2 wherein said molecular sieve following said contacting and separating steps is treated to remove said sorbed amide.

4. The process of claim 3 wherein the treating of said molecular sieve to remove sorbed amide is by heating in either an inert or reactive atmosphere and said molecular sieve thus treated is reused for further sorption of amide.

5. The process of claim 1 wherein said sorbed amide had 1 or 2 carbon atoms and said remaining amide has up to 10 carbon atoms.

6. The process of claim 1 wherein said molecular sieve is chabazite containing divalent cations.

7. The process of claim 6 wherein said chabazite is calcium chabazite.

8. The process of claim 1 wherein said sorbed amide is formamide, said remaining amide is N-(1-ethoxyethyl)formamide, and said molecular sieve is a NaX zeolite.

9. The process of claim 1 wherein said sorbed amide is formamide, said remaining amide is N-(1-alkoxyethyl)formamide, and said molecular sieve is a CaX zeolite.

10. The process of claim 1 wherein said sorbed amide is formamide, said remaining amide is N-vinylformamide, and said molecular sieve is a NaA zeolite.

11. The process of claim 1 wherein said sorbed amide is formamide, said remaining amide is N-methylformamide or N,N-dimethylformamide and said molecular sieve is a NaA zeolite.

12. The process of claim 1 wherein said sorbed amide is formamide, said remaining amide is N,N-dimethylformamide, and said molecular sieve is a type A zeolite containing sodium or calcium cations.

13. The process of claim 7 wherein said sorbed amide is N-methyl formamide and said remaining amide is N,N-dimethylformamide.

14. The process of claim 1 wherein said sorbed amide is acetamide, said remaining amide is N-methylacetamide, and said molecular sieve is a NaX zeolite.

15. A process for reducing the amount of formamide which is otherwise present in a product of N-vinylformamide prepared by a synthesis in which formamide is a starting reactant which comprises contacting a solution which contains residual formamid and either said N-vinylformamide or an amide precursor thereof with a cation-containing zeolite of types A, X, Y, molecular sieves of the MFI topology, chabazite or mordenite, thereby sorbing formamide in said zeolite; and separating said zeolite from said solution.

16. The process of claim 15 wherein said formamide is separated from a precursor of N-vinylformamide which is N-(1-methoxyethyl)formamide or N-(1-ethoxyethyl)formamide.

17. The process of claim 15 wherein said formamide is separated from N-vinylformamide.

18. The process of claim 15 wherein said zeolite is calcium chabazite.

19. The process of claim 15 wherein water is present in said solution at the initial contacting with said zeolite and is also sorbed in said zeolite.

* * * * *